United States Patent [19]

Payne et al.

[11] Patent Number: 5,723,758

[45] Date of Patent: Mar. 3, 1998

[54] BACILLUS THURINGIENSIS GENES ENCODING LEPIDOPTERAN-ACTIVE TOXINS

[75] Inventors: Jewel Payne, Davis, Calif.; David A. Cummings, Faversham; Raymond J.C. Cannon, Sittingbourne, both of England; Kenneth E. Narva; Steve Stelman, both of San Diego, Calif.

[73] Assignee: Mycogen Corporation, San Diego, Calif.

[21] Appl. No.: 448,170

[22] Filed: May 23, 1995

Related U.S. Application Data

[60] Continuation-in-part of Ser. No. 69,902, Jun. 1, 1993, abandoned, which is a division of Ser. No. 759,247, Sep. 13, 1991, Pat. No. 5,268,172.

[51] Int. Cl.[6] .............................. C12N 5/14; C12N 15/32
[52] U.S. Cl. ...................... 800/205; 435/252.3; 435/419; 536/23.71; 514/12
[58] Field of Search ....................... 536/23.71; 800/205; 435/240.1, 240.4, 252.3, 69.1, 325, 419; 574/12

[56] References Cited

U.S. PATENT DOCUMENTS

| | | | |
|---|---|---|---|
| 4,448,885 | 5/1984 | Schnepf et al. | 435/172.3 |
| 4,467,036 | 8/1984 | Schnepf et al. | 435/172.3 |
| 4,910,016 | 3/1990 | Gaertner et al. | 435/252.5 |
| 5,041,379 | 8/1991 | Fraser et al. | 435/235.1 |
| 5,063,055 | 11/1991 | Burges et al. | 435/69.1 |
| 5,064,648 | 11/1991 | Hickle et al. | 435/69.1 |
| 5,268,172 | 12/1993 | Payne et al. | 435/252.5 |
| 5,322,687 | 6/1994 | Donovan et al. | 536/23.71 |
| 5,430,137 | 7/1995 | Gaertner et al. | 536/24.32 |

FOREIGN PATENT DOCUMENTS 0142924  5/1985  European Pat. Off..

OTHER PUBLICATIONS

Dixon, B. (1991) "B.T. Toxins Studied" Bio/Technology 9:415.

Hickman, C.P. (1973) "Phylum Arthropoda–The Myriapods and Insects" Biology of the Invertebrates, pp. 621–622.

Kaichun, L. et al. (1990) "Applications of Shachongjin" in the Control of Pests of Horticulture I. The Effect of Shachongjin, a new *Bacillus thuringiensis*Agent, Againist the Larvae of *Apriona germari*(Coleoptera) 5th International Colloquium on Invertebrate Pathology and Microbial Control, Adelaide, Australia, Aug. 20–24, 1990, abstract no. 1133891.

Murray, E.E. et al. (1991) "Analysis of usntable RNA transcripts of insecticidal crystal protein genes of *Bacillus thuringiensis*in trangenic plants and electroporated protoplasts" Plant Molecular Biology 16:1035–1050.

Schnepf, H.E., H.R. Whiteley (1981) "Cloning and expression of the *Bacillus thuringiensis*crystal protein gene in *Escherichia coli*" Proc. Natl. Acad. Sci. USA 78(5):2893–2897.

Thorne, L. et al. (1986) "Structural Similarity between the Lepidoptera–and Diptera–Specific Insecticidal Endotoxin Genes of *Bacillus thuringiensis*subsp. kurstaki and israelensis" Journal of Bacteriology 166(3):801–811.

*Primary Examiner*—Che S. Chereskin
*Attorney, Agent, or Firm*—Saliwanchik, Lloyd & Saliwanchik

[57] ABSTRACT

Novel *B.t.* genes encoding toxins active against lepidopteran insects have been cloned from a novel lepidopteran-active *B. thuringiensis* microbe. The DNA encoding the *B.t.* toxin can be used to transform various hosts to express the *B.t.* toxin.

11 Claims, 2 Drawing Sheets

FIG. 1

A. *Bacillus thuringiensis* var. *kurstaki*
B. *Bacillus thuringiensis* var. *aizawai*
C. *Bacillus thuringiensis* PS158C2

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

GGACCAGGAT TTACAGGWGG RRA 23

( 2 ) INFORMATION FOR SEQ ID NO:2:

( i ) SEQUENCE CHARACTERISTICS:
( A ) LENGTH: 29 bases

-continued (B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:2:

TAACGTGTAT WCGSTTTTAA TTTWGAYTC    29

(2) INFORMATION FOR SEQ ID NO:3:

(i) SEQUENCE CHARACTERISTICS:
(A) LENGTH: 2154 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| ATGTGTGGGT | TTACCCCTAC | TAGAAGTCGA | GAACAAGTGG | CAGAAATTAG | TTTGGGGCTC | 60 |
| ACGCGTTTTC | TGTTGGAGAA | TCTTTTCCCA | GGTTCAACTT | TTGGATTTGG | TTTAATCGAT | 120 |
| ATTATTTGGG | GGATTTTTGG | GCCTGATCAA | TGGAGTATGT | TTCTGAACAA | ATTGAACAAC | 180 |
| TAATTGACCA | GAGAATAGAG | ACAGTCGAAA | GGAATAGGGC | AAATCAAACA | TTAATTGGGT | 240 |
| TATCAATAGT | TATGATGTAT | ATATTGAAGC | GTTAAAAGAA | TGGGAAAATA | ATCCTGATAA | 300 |
| TTCAGCTTCA | CAAGAAAGAG | TACGTAATCG | CTTTCGGACA | ACTGACGATG | CTTTGATAAC | 360 |
| TGGCATTCCT | CTTTTAGCCA | TTCCGAATTT | TGAAATAGCT | ACTTTATCGG | TGTATGTTCA | 420 |
| AGCTGCCAAT | CTACATTTAT | CCTTATTAAG | GGATGCAGTG | TTTTCGGAG | AAAGATGGGG | 480 |
| ATTAACACAA | ATAAATGTAG | ATGACTTGTA | CAGGAGATTA | ACGAATAATA | TCAGAACTAA | 540 |
| TTCAGATCAT | TGTGCACGAT | GGTATAATGA | AGGATTAGAT | AATATTTCTG | GTTTATCTCG | 600 |
| ATCTATTAAC | TTCCAAAGAG | AAGTAACAAT | CTCTGTCTTA | GATATTGTTG | CGCTTTTCCC | 660 |
| GAACTATGAC | ATCCGAACAT | ATCCAATTTC | AACAACAAGC | CAATTAACAA | GGGAGATATT | 720 |
| CACATCTCCA | ATTGTTGTCC | CTAATGATTT | TAGTGTAGCC | TACGAGGGGG | TAAGGAGAGC | 780 |
| GCCACACCTA | TTTGAATTTT | TAGAGAAACT | TGTTATTTAT | ACCGGTGATC | GAAGTGGGAT | 840 |
| TCGCCATTGG | GCGGGACATG | AAATAACTTC | TAGACGTACT | GATTCATACC | ACGGTATAAT | 900 |
| TCGTTACCCT | CTTTATGGAA | CAGCAGCAAA | TGCAGAAAGT | CCATATACTC | TTGCCCTTCA | 960 |
| ACCTTCTGGA | AGTATTTATA | GAACGTTATC | AGAACCTATA | TTTTCACAAA | CTGGTGGGCT | 1020 |
| GTCTCCTCAT | AGAAGGAGAG | TAGTAGAGGG | AGTAGAGTTC | TCTATTGTAA | ATAATAACGT | 1080 |
| AAATCCTTCG | TCATTTGTAT | ATAGAAGAAA | GGGTTCGTTA | GATTCTTTTA | CTGAGTTACC | 1140 |
| ACCTGAAGAT | GAAAGTGTAC | CACCTTATAT | TGGCTACAGT | CATCAATTAT | GCCATGTTGG | 1200 |
| ATTGGTCGT | ACAAATGTAA | TCTTTGAACC | AAGTAATTTC | GCTAGGGTTC | CAGTATTCTC | 1260 |
| CTGGACACAT | CGTAGTGCAA | CCCCTACAAA | TACAATTGAT | CCAGATAGAA | TTACCCAAAT | 1320 |
| ACCTTCAGTG | AAGGCGAGTT | CTCTTCGTAA | TTCTACTGTT | GTTAGTGGAC | CAGGATTTAC | 1380 |
| TGGAGGGGAT | ATTGTTCGAA | TGGGAGCAGT | GCACCAAATA | TATGCACGGA | TTTAAGTATG | 1440 |
| AATGTTCGAC | CTAGTGTTGC | ATTGAGCAGA | TATCTTATAA | GACTTCGCTA | TGCTTGTAGG | 1500 |
| GGGAGTTCAA | ACATAGTTAT | ACACGGTCCT | TCTATTAGAT | TTGTATCGCT | CCCAAGTACA | 1560 |
| ATGAGTAATG | ATGAACCTTT | AACATATCAA | TCATTTAGAT | ACGCAAGTAT | CACAACTCCA | 1620 |
| ATTACCCGTC | CAATATATAA | CATGTTTAAT | TTATCTATAT | CCAGAATTTC | AGGTGTCCAA | 1680 |
| AATTTGTTTA | TAGATCGAAT | AGAATTCATT | CCAGTAGATG | CAAACTTCGA | AGCAGAACGA | 1740 |

```
GATTTAGAGA GAGCGCAGAA GGCGGTGAAT GCTCTGTTTA CTTCCACAAA CCAAAAGGAT      1800

AAAAAGATG  TGACGATATC  ATATTGATCA  AGTTCCAATT  TAGTTGTGTT  ATCGGATAAT      1860

TTGTCTGGAT GAAAAGCGAG AATTGTCCGA AAAAAACATG CGAAGCGACT CAGTGATGAG         1920

AATTTACTCC AAGATAAAAC TTTACAGGCA TCAATAGGCA AGTAGACCGT GGGTGGAGAG         1980

GAAGTACGGA TATTACCATC CAAGGAGGGA ATGATGTATT CAAAGAGAAT TACGTCACAC         2040

TACCAGGTAC CTTTGATGAG TGTTACCCAA CGTATTTGTA TCAAAAAATA GATGAGTCAA         2100

AATTAAAACC TATACTCGCT ATGAATTAAG AGGGTATATT GAAGATAGTC AAGA              2154
```

( 2 ) INFORMATION FOR SEQ ID NO:4:

( i ) SEQUENCE CHARACTERISTICS:
        ( A ) LENGTH: 725 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Cys Gly Phe Thr Pro Thr Arg Ser Arg Glu Gln Val Ala Glu Ile
 1               5                  10                  15

Ser Leu Gly Leu Thr Arg Phe Leu Leu Glu Asn Leu Phe Pro Gly Ser
             20                  25                  30

Thr Phe Gly Phe Gly Leu Ile Asp Ile Ile Trp Gly Ile Phe Gly Pro
         35                  40                  45

Asp Gln Trp Ser Met Phe Xaa Glu Gln Ile Glu Gln Leu Ile Asp Gln
     50                  55                  60

Arg Ile Glu Thr Val Glu Arg Asn Arg Ala Asn Xaa Asn Ile Asn Trp
 65                  70                  75                  80

Val Ile Asn Ser Tyr Asp Val Tyr Ile Glu Ala Leu Lys Glu Trp Glu
                 85                  90                  95

Asn Asn Pro Asp Asn Ser Ala Ser Gln Glu Arg Val Arg Asn Arg Phe
            100                 105                 110

Arg Thr Thr Asp Asp Ala Leu Ile Thr Gly Ile Pro Leu Leu Ala Ile
        115                 120                 125

Pro Asn Phe Glu Ile Ala Thr Leu Ser Val Tyr Val Gln Ala Ala Asn
    130                 135                 140

Leu His Leu Ser Leu Leu Arg Asp Ala Val Phe Phe Gly Glu Arg Trp
145                 150                 155                 160

Gly Leu Thr Gln Ile Asn Val Asp Asp Leu Tyr Arg Arg Leu Thr Asn
                165                 170                 175

Asn Ile Arg Thr Asn Ser Asp His Cys Ala Arg Trp Tyr Asn Glu Gly
            180                 185                 190

Leu Asp Asn Ile Ser Gly Leu Ser Arg Ser Ile Asn Phe Gln Arg Glu
        195                 200                 205

Val Thr Ile Ser Val Leu Asp Ile Val Ala Leu Phe Pro Asn Tyr Asp
    210                 215                 220

Ile Arg Thr Tyr Pro Ile Ser Thr Thr Ser Gln Leu Thr Arg Glu Ile
225                 230                 235                 240

Phe Thr Ser Pro Ile Val Val Pro Asn Asp Phe Ser Val Ala Tyr Glu
                245                 250                 255

Gly Val Arg Arg Ala Pro His Leu Phe Glu Phe Leu Glu Lys Leu Val
            260                 265                 270

Ile Tyr Thr Gly Asp Arg Ser Gly Ile Arg His Trp Ala Gly His Glu
```

-continued

|     |     |     |     | 275 |     |     |     |     | 280 |     |     |     |     | 285 |     |
| --- | --- | --- | --- | --- | --- | --- | --- | --- | --- | --- | --- | --- | --- | --- | --- |

Ile Thr Ser Arg Arg Thr Asp Ser Tyr His Gly Ile Ile Arg Tyr Pro
290                     295                 300

Leu Tyr Gly Thr Ala Ala Asn Ala Glu Ser Pro Tyr Thr Leu Ala Leu
305                     310                 315                     320

Gln Pro Ser Gly Ser Ile Tyr Arg Thr Leu Ser Glu Pro Ile Phe Ser
                    325                     330                     335

Gln Thr Gly Gly Leu Ser Pro His Arg Arg Arg Val Val Glu Gly Val
                    340                     345                 350

Glu Phe Ser Ile Val Asn Asn Asn Val Asn Pro Ser Ser Phe Val Tyr
            355                     360                 365

Arg Arg Lys Gly Ser Leu Asp Ser Phe Thr Glu Leu Pro Pro Glu Asp
        370                     375                 380

Glu Ser Val Pro Pro Tyr Ile Gly Tyr Ser His Gln Leu Cys His Val
385                     390                     395                     400

Gly Phe Gly Arg Thr Asn Val Ile Phe Glu Pro Ser Asn Phe Ala Arg
                    405                     410                 415

Val Pro Val Phe Ser Trp Thr His Arg Ser Ala Thr Pro Thr Asn Thr
                420                     425                 430

Ile Asp Pro Asp Arg Ile Thr Gln Ile Pro Ser Val Lys Ala Ser Ser
            435                     440                 445

Leu Arg Asn Ser Thr Val Val Ser Gly Pro Gly Phe Thr Gly Gly Asp
    450                     455                 460

Ile Val Arg Met Gly Ala Val His Gln Ile Tyr Ala Xaa Asp Leu Ser
465                     470                     475                     480

Met Asn Val Arg Pro Ser Val Ala Leu Ser Arg Tyr Leu Ile Arg Leu
                485                     490                 495

Arg Tyr Ala Cys Arg Gly Ser Ser Asn Ile Val Ile His Gly Pro Ser
                500                     505                 510

Ile Arg Phe Val Ser Leu Pro Ser Thr Met Ser Asn Asp Glu Pro Leu
            515                     520                 525

Thr Tyr Gln Ser Phe Arg Tyr Ala Ser Ile Thr Thr Pro Ile Thr Arg
    530                     535                 540

Pro Ile Tyr Asn Met Phe Asn Leu Ser Ile Ser Arg Ile Ser Gly Val
545                     550                     555                     560

Gln Asn Leu Phe Ile Asp Arg Ile Glu Phe Ile Pro Val Asp Ala Asn
                565                     570                 575

Phe Glu Ala Glu Arg Asp Leu Glu Arg Ala Gln Lys Ala Val Asn Ala
                580                     585                 590

Leu Phe Thr Ser Thr Asn Gln Xaa Gly Leu Lys Xaa Asp Val Thr Asp
    595                     600                 605

Tyr His Ile Asp Gln Val Ser Asn Leu Val Xaa Cys Leu Ser Asp Xaa
    610                     615                 620

Phe Cys Leu Asp Glu Lys Arg Glu Leu Ser Glu Lys Xaa Lys His Ala
625                     630                     635                     640

Lys Arg Leu Ser Asp Glu Xaa Asn Leu Leu Gln Asp Xaa Asn Phe Thr
                645                     650                 655

Gly Ile Asn Arg Gln Val Asp Arg Gly Trp Arg Gly Ser Thr Asp Ile
                660                     665                 670

Thr Ile Gln Gly Gly Asn Asp Val Phe Lys Glu Asn Tyr Val Thr Leu
        675                     680                 685

Pro Gly Thr Phe Asp Glu Cys Tyr Pro Thr Tyr Leu Tyr Gln Lys Ile
690                     695                     700

|  |  |  |  |  |  |  |  |  |  |  |  |  |  |
|---|---|---|---|---|---|---|---|---|---|---|---|---|---|
| Asp | Glu | Ser | Lys | Leu | Lys | Pro | Xaa | Thr | Arg | Tyr | Glu | Leu | Arg | Gly | Tyr |
| 705 |  |  |  |  | 710 |  |  |  | 715 |  |  |  |  | 720 |

Ile Glu Asp Ser Gln
                725

( 2 ) INFORMATION FOR SEQ ID NO:5:

( i ) SEQUENCE CHARACTERISTICS:
        ( A ) LENGTH: 3501 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ATGGAGATAA ATAATCAGAA CCAATGCATA CCATATAATT GCTTAAGTAA TCCTGAGGAA    60
GTATTTTTGG ATGGGGAGAG GATATTACCT GATATCGATC CACTCGAAGT TTCTTTGTCG   120
CTTTTGCAAT TTCTTTTGAA TAACTTTGTT CCAGGGGGGG GGTTTATTTC AGGATTACTT   180
GATAAAATAT GGGGGGCTTT GAGACCATCT GATTGGGAAT TATTTCTTGA ACAGATTGAA   240
CAGTTGATTG ATCGAAGAAT AGAAGAACA GTAAGAGCAA AGCAATCGC TGAATTAGAA    300
GGTTTAGGGA GAAGTTATCA ACTATATGGA GAGGCATTTA AAGAGTGGGA AAAAACTCCA   360
GATAACACAC GGCTCGGTCT AGAGTAACTG AGAGATTTCG TATAATTGAT GCTCAATTGA   420
AGCAAATATC CCTTCGTTTC GGGTTTCCGG ATTTGAAGTG CCACTTCTAT TGGTTTATAC   480
CCAAGCAGCT AATTTGCATC TCGCTCTATT AAGAGATTCT GTTGTTTTTG GAGAGAGATG   540
GGGATTGACG ACTACAAATG TCAATGATAT CTATAATAGA CAAGTTAATA GAATTGGTGA   600
ATATAGCAAG CATTGTGTAG ATACGTATAA AACAGAATTA GAACGTCTAG GATTTAGATC   660
TATAGCGCAA TGGAGAATAT ATAATCAGTT TAGAAGGGAA TTGACACTAA CGGTATTAGA   720
TATTGTCGCT GTTTTCCCGA ACTATGATAG TAGACTGTAT CCGATTCGAA CAATTTCTCA   780
ATTGACAAGA GAAATTTATA CATCCCCAGT AAGCGAATTT TATTATGGTG TCATTAATAG   840
TAATAATATA ATTGGTACCC TTACTGAACA GCAAATAAGG CGACCACATC TTATGGACTT   900
CTTTAACTCC ATGATCATGT ATACGTCAGA TAATAGACGA GAACATTATT GGTCAGGACT   960
TGAAATGACG GCTACTAATA CTGAGGGACA TCAAAGGTCA TTCCCTTTAG CTGGGACTAT  1020
AGGGAATTCA GCTCCACCAG TAACTGTTAG AAATAATGGT GAGGGAATTT ATAGAATATT  1080
ATCGGAACCA TTTTATTCAG CACCTTTTCT AGGCACAAGT GTGCTAGGAA GTCGTGGGGA  1140
AGAATTTGCT TTTGCATCTA ATACTACTAC AAGTCTGCCA TCTACAATAT ATAGAAATCG  1200
TGGAACAGTA GATTCATTAG TCAGCATACC GCCACAGGAT TATAGCGTAC CACCGCACAG  1260
GGGGTATAGT CATTTATTAA GTCACGTTAC GATGCGCAAT AGTTCTCCTA TATTCCACTG  1320
GACACATCGT AGTGCAACCC CTAGAAATAC AATTGATCCA GATAGTATCA CTCAAATTCC  1380
AGCAGTTAAG GGAGCGTATA TTTTTAATAG TCCAGTCATT ACTGGGCCAG ACATACAGG   1440
TGGGGATATA ATAAGGTTTA ACCCTAATAC TCAGAACAAC ATAAGAATTC CATTTCAATC  1500
AAATGCGGTA CAGCGTTATC GAATTAGAAT GCGTTATGCG GCAGAAGCTG ATTGTATTTT  1560
AGAAAGTGGA GTAAACATTG TTACTGGGGC AGGGGTCACC TTTAGGCCAA TTCCTATTAA  1620
AGCTACAATG ACTCCTGGAA GTCCTTTAAC ATATTACAGC TTCCAGTATG CAGATTTAAA  1680
TATAAATCTT ACTGCGCCGA TAAGACCTAA TAATTTTGTA TCTATTAGAC GTTCAAACCA  1740
ACCAGGAAAC CTTTATATAG ATAGAATTGA ATTCATTCCA ATTGACCCAA TCCGTGAGGC  1800
AGAACATGAT TTAGAAAGAG CGCAAAAGGC GGTGAATGCG CTGTTTACTT CTTCCAATCA  1860
```

-continued

```
ACTAGGATTA AAAACAGATG TGACGGATTA TCATATTGAT CAAGTGTCCA ATTTAGTTGC      1920
GTGTTTATCG GATAAATTCT GCCTGGATGA AAAGCGAGAA TTGTCCGAGA AAGTTAAACA      1980
TGCGAAGCGA CTCAGTGATG AGAGAAATTT ACTCCAAGAT CAAAACTTTA CAGGCATCAA      2040
TAGGCAAGTA GACCGTGGGT GGAGAGGAAG TACGGATATT ACCACCCAAG GAGGGAATGA      2100
TGTATTCAAA GAGAATTACG TCACACTACC AGGTACCTTT GATGAGTGTT ACCCAACGTA      2160
TTTGTATCAA AAAATAGATG AGTCAAAATT AAAACCTTAT ACTCGCTATG AATTAAGAGG      2220
GTATATTGAA GATAGTCAAG ACTTAGAAGT CTATTTGATC CGTTACAATG CAAAACACGA      2280
AACGTTAAAT GTGCCAGGTA CGGGTTCCTT ATGGCCACTT GCAGCCGAAA GTTCAATCGG      2340
GAGGTGCGGC GAACCGAATC GATGCGCGCC ACATATTGAA TGGAATCCTG AACTAGATTG      2400
TTCGTGTAGG GATGGAGAAA AATGTGCACA TCATTCTCAT CATTTCTCCT TGGATATTGA      2460
TGTTGGATGT ACAGACTTAA ATGAGGATTT AGGTGTATGG GTGATATTTA AGATTAAGAC      2520
GCAAGATGGC TATGCAAGAC TAGGAAATTT AGAGTTTCTC GAAGAGAAAC CATTGTTAGG      2580
AGAAGCGCTA GCTCGTGTGA AGAGAGCGGA GAAAAATGG AGAGACAAAC GCGACAAATT       2640
GGATGGAAAC AAATATTGTT TATAAAGAGC CAAAGAATCT GTAGATGCTT TATCGTAGAT      2700
TCTCAATATA ATAGATTACA ACCGGATACG AACATTGCGA TGATTCATGT GGCAGATAAA      2760
CGCGTTCATC GAATCCGAGA AGCGTATTTG CCAGAGTTAT CTGTGATTCC GGGTGTCAAT      2820
GCGGCTATTT TCGAAGAATT AGAAGGTCTT ATTTTCACTG CATTCTCCCT ATATGATGCG      2880
AGAAATGTCA TTAAAAACGG AGATTTCAAT CATGGTTTAT CATGCTGGAA CGTGAAAGGG      2940
CATGTAGATG TAGAAGAACA AAATAACCAC CGTTCGGTCC TTGTTGTTCC GGAATGGGAA      3000
GCAGAAGTGT CACAAGAAGT CCGCGTATGT CCAGGACGTG GCTATATCCT GCGTGTTACA      3060
GCGTACAAAG AGGGCTACGG AGAAGGATGC GTAACGATCC ATGAAATTGA AGATCATACA      3120
GACGAACTGA AATTTAGAAA CTGTGAAGAA GAGGAAGTGT ATCCGAATAA CACGGTAACG      3180
TGTAATGATT ATCCAGCAAA TCAAGAAGAA TACAGGGCTG CGGAAACTTC CCGTAATCGT      3240
GGATATGGCG AATCTTATGA AAGTAATTCT TCCATACCAG CTGAGTATGC GCCAATTTAT      3300
GAGAAAGCAT ATACAGATGG AAGAAAAGAG AATTCTTGTG AATCTAACAG AGGATATGGA      3360
AATTACACAC CGTTACCAGC AGGTTATGTG ACAAAAGAAT AGAGTACTT CCCAGAAACC       3420
GATAAGGTAT GGATAGAGAT TGGAGAAACG GAAGGAACAT TCATCGTAGA CAGTGTGGAA      3480
TTACTCCTCA TGGAGGAATA G                                               3501
```

( 2 ) INFORMATION FOR SEQ ID NO:6:

( i ) SEQUENCE CHARACTERISTICS:
        ( A ) LENGTH: 1168 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Met Glu Ile Asn Asn Gln Asn Gln Cys Ile Pro Tyr Asn Cys Leu Ser
 1               5                  10                  15

Asn Pro Glu Glu Val Phe Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Leu Asp Lys Ile Trp
```

```
               50                         55                         60

Gly  Ala  Leu  Arg  Pro  Ser  Asp  Trp  Glu  Leu  Phe  Leu  Glu  Gln  Ile  Glu
   65                  70                       75                            80

Gln  Leu  Ile  Asp  Arg  Arg  Ile  Glu  Arg  Thr  Val  Arg  Ala  Lys  Ala  Ile
                       85                       90                       95

Ala  Glu  Leu  Glu  Gly  Leu  Gly  Arg  Ser  Tyr  Gln  Leu  Tyr  Gly  Glu  Ala
                  100                      105                      110

Phe  Lys  Glu  Trp  Glu  Lys  Thr  Pro  Asp  Asn  Thr  Xaa  Ala  Arg  Ser  Arg
             115                      120                      125

Val  Thr  Glu  Arg  Phe  Arg  Ile  Ile  Asp  Ala  Xaa  Ile  Glu  Ala  Asn  Ile
        130                      135                      140

Pro  Ser  Phe  Arg  Val  Ser  Gly  Phe  Glu  Val  Pro  Leu  Leu  Val  Tyr
   145                      150                      155                      160

Thr  Gln  Ala  Ala  Asn  Leu  His  Leu  Ala  Leu  Leu  Arg  Asp  Ser  Val  Val
                       165                      170                      175

Phe  Gly  Glu  Arg  Trp  Gly  Leu  Thr  Thr  Thr  Asn  Val  Asn  Asp  Ile  Tyr
                  180                      185                      190

Asn  Arg  Gln  Val  Asn  Arg  Ile  Gly  Glu  Tyr  Ser  Lys  His  Cys  Val  Asp
             195                      200                      205

Thr  Tyr  Lys  Thr  Glu  Leu  Glu  Arg  Leu  Gly  Phe  Arg  Ser  Ile  Ala  Gln
        210                      215                      220

Trp  Arg  Ile  Tyr  Asn  Gln  Phe  Arg  Arg  Glu  Leu  Thr  Leu  Thr  Val  Leu
   225                      230                      235                      240

Asp  Ile  Val  Ala  Val  Phe  Pro  Asn  Tyr  Asp  Ser  Arg  Leu  Tyr  Pro  Ile
                       245                      250                      255

Arg  Thr  Ile  Ser  Gln  Leu  Thr  Arg  Glu  Ile  Tyr  Thr  Ser  Pro  Val  Ser
                  260                      265                      270

Glu  Phe  Tyr  Tyr  Gly  Val  Ile  Asn  Ser  Asn  Asn  Ile  Ile  Gly  Thr  Leu
             275                      280                      285

Thr  Glu  Gln  Gln  Ile  Arg  Arg  Pro  His  Leu  Met  Asp  Phe  Phe  Asn  Ser
        290                      295                      300

Met  Ile  Met  Tyr  Thr  Ser  Asp  Asn  Arg  Arg  Glu  His  Tyr  Trp  Ser  Gly
   305                      310                      315                      320

Leu  Glu  Met  Thr  Ala  Thr  Asn  Thr  Glu  Gly  His  Gln  Arg  Ser  Phe  Pro
                       325                      330                      335

Leu  Ala  Gly  Thr  Ile  Gly  Asn  Ser  Ala  Pro  Pro  Val  Thr  Val  Arg  Asn
                  340                      345                      350

Asn  Gly  Glu  Gly  Ile  Tyr  Arg  Ile  Leu  Ser  Glu  Pro  Phe  Tyr  Ser  Ala
             355                      360                      365

Pro  Phe  Leu  Gly  Thr  Ser  Val  Leu  Gly  Ser  Arg  Gly  Glu  Glu  Phe  Ala
        370                      375                      380

Phe  Ala  Ser  Asn  Thr  Thr  Thr  Ser  Leu  Pro  Ser  Thr  Ile  Tyr  Arg  Asn
   385                      390                      395                      400

Arg  Gly  Thr  Val  Asp  Ser  Leu  Val  Ser  Ile  Pro  Pro  Gln  Asp  Tyr  Ser
                       405                      410                      415

Val  Pro  Pro  His  Arg  Gly  Tyr  Ser  His  Leu  Leu  Ser  His  Val  Thr  Met
                  420                      425                      430

Arg  Asn  Ser  Ser  Pro  Ile  Phe  His  Trp  Thr  His  Arg  Ser  Ala  Thr  Pro
             435                      440                      445

Arg  Asn  Thr  Ile  Asp  Pro  Asp  Ser  Ile  Thr  Gln  Ile  Pro  Ala  Val  Lys
        450                      455                      460

Gly  Ala  Tyr  Ile  Phe  Asn  Ser  Pro  Val  Ile  Thr  Gly  Pro  Gly  His  Thr
   465                      470                      475                      480
```

```
Gly Gly Asp Ile Ile Arg Phe Asn Pro Asn Thr Gln Asn Asn Ile Arg
            485             490                 495

Ile Pro Phe Gln Ser Asn Ala Val Gln Arg Tyr Arg Ile Arg Met Arg
        500             505             510

Tyr Ala Ala Glu Ala Asp Cys Ile Leu Glu Ser Gly Val Asn Ile Val
        515             520             525

Thr Gly Ala Gly Val Thr Phe Arg Pro Ile Pro Ile Lys Ala Thr Met
    530             535             540

Thr Pro Gly Ser Pro Leu Thr Tyr Tyr Ser Phe Gln Tyr Ala Asp Leu
545             550             555             560

Asn Ile Asn Leu Thr Ala Pro Ile Arg Pro Asn Asn Phe Val Ser Ile
            565             570             575

Arg Arg Ser Asn Gln Pro Gly Asn Leu Tyr Ile Asp Arg Ile Glu Phe
            580             585             590

Ile Pro Ile Asp Pro Ile Arg Glu Ala His Asp Leu Glu Arg Ala
        595             600             605

Gln Lys Ala Val Asn Ala Leu Phe Thr Ser Ser Asn Gln Leu Gly Leu
        610             615             620

Lys Thr Asp Val Thr Asp Tyr His Ile Asp Gln Val Ser Asn Leu Val
625             630             635             640

Ala Cys Leu Ser Asp Lys Phe Cys Leu Asp Glu Lys Arg Glu Leu Ser
            645             650             655

Glu Lys Val Lys His Ala Lys Arg Leu Ser Asp Glu Arg Asn Leu Leu
            660             665             670

Gln Asp Gln Asn Phe Thr Gly Ile Asn Arg Gln Val Asp Arg Gly Trp
            675             680             685

Arg Gly Ser Thr Asp Ile Thr Thr Gln Gly Gly Asn Asp Val Phe Lys
    690             695             700

Glu Asn Tyr Val Thr Leu Pro Gly Thr Phe Asp Glu Cys Tyr Pro Thr
705             710             715             720

Tyr Leu Tyr Gln Lys Ile Asp Glu Ser Lys Leu Lys Pro Tyr Thr Arg
            725             730             735

Tyr Glu Leu Arg Gly Tyr Ile Glu Asp Ser Gln Asp Leu Glu Val Tyr
            740             745             750

Leu Ile Arg Tyr Asn Ala Lys His Glu Thr Leu Asn Val Pro Gly Thr
        755             760             765

Gly Ser Leu Trp Pro Leu Ala Ala Glu Ser Ser Ile Gly Arg Cys Gly
    770             775             780

Glu Pro Asn Arg Cys Ala Pro His Ile Glu Trp Asn Pro Glu Leu Asp
785             790             795             800

Cys Ser Cys Arg Asp Gly Glu Lys Cys Ala His His Ser His His Phe
            805             810             815

Ser Leu Asp Ile Asp Val Gly Cys Thr Asp Leu Asn Glu Asp Leu Gly
        820             825             830

Val Trp Val Ile Phe Lys Ile Lys Thr Gln Asp Gly Tyr Ala Arg Leu
        835             840             845

Gly Asn Leu Glu Phe Leu Glu Glu Lys Pro Leu Leu Gly Glu Ala Leu
    850             855             860

Ala Arg Val Lys Arg Ala Glu Lys Lys Trp Arg Asp Lys Arg Asp Lys
865             870             875             880

Leu Xaa Trp Xaa Thr Asn Ile Val Tyr Lys Glu Xaa Lys Glu Ser Val
            885             890             895

Asp Ala Leu Xaa Val Asp Ser Gln Tyr Asn Arg Leu Gln Pro Asp Thr
            900             905             910
```

| | | | | | | | | | | | | | | |
|---|---|---|---|---|---|---|---|---|---|---|---|---|---|---|
|Asn|Ile|Ala|Met|Ile|His|Val|Ala|Asp|Lys|Arg|Val|His|Arg|Ile|Arg|
| | |915| | | | |920| | | |925| | | |
|Glu|Ala|Tyr|Leu|Pro|Glu|Leu|Ser|Val|Ile|Pro|Gly|Val|Asn|Ala|Ala|
| |930| | | | |935| | | |940| | | | |
|Ile|Phe|Glu|Glu|Leu|Glu|Gly|Leu|Ile|Phe|Thr|Ala|Phe|Ser|Leu|Tyr|
|945| | | | |950| | | | |955| | | | |960|
|Asp|Ala|Arg|Asn|Val|Ile|Lys|Asn|Gly|Asp|Phe|Asn|His|Gly|Leu|Ser|
| | | | |965| | | | |970| | | | |975| |
|Cys|Trp|Asn|Val|Lys|Gly|His|Val|Asp|Val|Glu|Glu|Gln|Asn|Asn|His|
| | | |980| | | | |985| | | | |990| | |
|Arg|Ser|Val|Leu|Val|Val|Pro|Glu|Trp|Glu|Ala|Glu|Val|Ser|Gln|Glu|
| | |995| | | | |1000| | | | |1005| | | |
|Val|Arg|Val|Cys|Pro|Gly|Arg|Gly|Tyr|Ile|Leu|Arg|Val|Thr|Ala|Tyr|
| |1010| | | | |1015| | | | |1020| | | | |
|Lys|Glu|Gly|Tyr|Gly|Glu|Gly|Cys|Val|Thr|Ile|His|Glu|Ile|Glu|Asp|
|1025| | | | |1030| | | | |1035| | | | |1040|
|His|Thr|Asp|Glu|Leu|Lys|Phe|Arg|Asn|Cys|Glu|Glu|Glu|Glu|Val|Tyr|
| | | | |1045| | | | |1050| | | | |1055| |
|Pro|Asn|Asn|Thr|Val|Thr|Cys|Asn|Asp|Tyr|Pro|Ala|Asn|Gln|Glu|Glu|
| | | |1060| | | | |1065| | | | |1070| | |
|Tyr|Arg|Ala|Ala|Glu|Thr|Ser|Arg|Asn|Arg|Gly|Tyr|Gly|Glu|Ser|Tyr|
| | |1075| | | | |1080| | | | |1085| | | |
|Glu|Ser|Asn|Ser|Ser|Ile|Pro|Ala|Glu|Tyr|Ala|Pro|Ile|Tyr|Glu|Lys|
| |1090| | | | |1095| | | | |1100| | | | |
|Ala|Tyr|Thr|Asp|Gly|Arg|Lys|Glu|Asn|Ser|Cys|Glu|Ser|Asn|Arg|Gly|
|1105| | | | |1110| | | | |1115| | | | |1120|
|Tyr|Gly|Asn|Tyr|Thr|Pro|Leu|Pro|Ala|Gly|Tyr|Val|Thr|Lys|Glu|Leu|
| | | | |1125| | | | |1130| | | | |1135| |
|Glu|Tyr|Phe|Pro|Glu|Thr|Asp|Lys|Val|Trp|Ile|Glu|Ile|Gly|Glu|Thr|
| | | |1140| | | | |1145| | | | |1150| | |
|Glu|Gly|Thr|Phe|Ile|Val|Asp|Ser|Val|Glu|Leu|Leu|Leu|Met|Glu|Glu|
| | |1155| | | | |1160| | | | |1165| | | |

( 2 ) INFORMATION FOR SEQ ID NO:7:

( i ) SEQUENCE CHARACTERISTICS:
        ( A ) LENGTH: 3684 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
TTGACTTCAA ATAGGAAAAA TGAGAATGAA ATTATAAATG CTTTATCGAT TCCAGCTGTA      60
TCGAATCATT CCGCACAAAT GAATCTATCA ACCGATGCTC GTATTGAGGA TAGCTTGTGT     120
ATAGCCGAGG GGAACAATAT CGATCCATTT GTTAGCGCAT CAACAGTCCA AACGGGTATT     180
AACATAGCTG GTAGAATACT AGGTGTATTA GGCGTACCGT TGCTGGACA  AATAGCTAGT     240
TTTTATAGTT TTCTTGTTGG TGAATTATGG CCCCGCGGCA GAGATCCTTG GGAAATTTTC     300
CTAGAACATG TCGAACAACT TATAAGACAA CAAGTAACAG AAAATACTAG GGATACGGCT     360
CTTGCTCGAT TACAAGGTTT AGGAAATTCC TTTAGAGCCT ATCAACAGTC ACTTGAAGAT     420
TGGCTAGAAA ACCGTGATGA TGCAAGAACG AGAAGTGTTC TTTATACCCA ATATATAGCC     480
TTAGAACTTG ATTTTCTTAA TGCGATGCCG CTTTTCGCAA TTAGAAACCA AGAAGTTCCA     540
```

-continued

```
TTATTAATGG TATATGCTCA AGCTGCAAAT TTACACCTAT TATTATTGAG AGATGCCTCT    600
CTTTTTGGTA GTGAATTTGG GCTTACATCC CAAGAAATTC AACGTTATTA TGAGCGCCAA    660
GTGGAAAAAA CGAGAGAATA TTCTGATTAT TGCGCAAGAT GGTATAATAC GGGTTTAAAT    720
AATTTGAGAG GACAAATGC  TGAAAGTTGG TTGCGATATA ATCAATTCCG TAGAGACTTA    780
ACGCTAGGAG TATTAGATCT AGTGGCACTA TTCCCAAGCT ATGACACGCG TGTTTATCCA    840
ATGAATACCA GTGCTCAATT AACAAGAGAA ATTTATACAG ATCCAATTGG GAGAACAAAT    900
GCACCTTCAG GATTTGCAAG TACGAATTGG TTTAATAATA ATGCACCATC GTTTCTGCC     960
ATAGAGGCTG CCGTTATTAG GCCTCCGCAT CTACTTGATT TTCCAGAACA GCTTACAATT   1020
TTCAGCGTAT TAAGTCGATG GAGTAATACT CAATATATGA ATTACTGGGT GGGACATAGA   1080
CTTGAATCGC GAACAATAAG GGGGTCATTA AGTACCTCGA CACACGGAAA TACCAATACT   1140
TCTATTAATC CTGTAACATT ACAGTTCACA TCTCGAGACG TTTATAGAAC AGAATCATTT   1200
GCAGGGATAA ATATACTTCT AACTACTCCT GTGAATGGAG TACCTTGGGC TAGATTTAAT   1260
TGGAGAAATC CCCTGAATTC TCTTAGAGGT AGCCTTCTCT ATACTATAGG GTATACTGGA   1320
GTGGGGACAC AACTATTTGA TTCAGAAACT GAATTACCAC CAGAAACAAC AGAACGACCA   1380
AATTATGAAT CTTACAGTCA TAGATTATCT AATATAAGAC TAATATCAGG AAACACTTTG   1440
AGAGCACCAG TATATTCTTG GACGCACCGT AGTGCAGATC GTACAAATAC CATTAGTTCA   1500
GATAGCATAA CACAAATACC ATTGGTAAAA TCATTCAACC TTAATTCAGG TACCTCTGTA   1560
GTCAGTGGCC CAGGATTTAC AGGAGGGGAT ATAATCCGAA CTAACGTTAA TGGTAGTGTA   1620
CTAAGTATGG GTCTTAATTT TAATAATACA TCATTACAGC GGTATCGCGT GAGAGTTCGT   1680
TATGCTGCTT CTCAAACAAT GGTCCTGAGG GTAACTGTCG GAGGGAGTAC TACTTTTGAT   1740
CAAGGATTCC CTAGTACTAT GAGTGCAAAT GAGTCTTTGA CATCTCAATC ATTTAGATTT   1800
GCAGAATTTC CTGTAGGTAT TAGTGCATCT GGCAGTCAAA CTGCTGGAAT AAGTATAAGT   1860
AATAATGCAG GTAGACAAAC GTTTCACTTT GATAAAATTG AATTCATTCC AATTACTGCA   1920
ACCTTCGAAG CAGAATATGA TTTAGAAAGA GCGCAAGAGG CGGTGAATGC TCTGTTTACT   1980
AATACGAATC CAAGAAGGTT GAAAACAGGT GTGACAGATT ATCATATTGA TGAAGTATCC   2040
AATTTAGTGG CGTGTTTATC GGATGAATTC TGCTTGGATG AAAAGAGAGA ATTACTTGAG   2100
AAAGTGAAAT ATGCGAAACG ACTCAGTGAT GAAAGAAACT TACTCCAAGA TCCAAACTTC   2160
ACATCCATCA ATAAGCAACC AGACTTCATA TCTACTAATG AGCAATCGAA TTTCACATCT   2220
ATCCATGAAC AATCTGAACA TGGATGGTGG GGAAGTGAGA ACATTACAAT CCAGGAAGGA   2280
AATGACGTAT TTAAAGAGAA TTACGTCATA CTACCGGGTA CTTTTAATGA GTGTTATCCG   2340
ACGTATTTAT ATCAAAAAAT AGGGGAGGCG GAATTAAAAG CTTATACTCG CTACCAATTA   2400
AGTGGCTATA TTGAAGATAG TCAAGATTTA GAGATATATT TGATTCGTTA CAATGCGAAA   2460
CATGAAACAT TGGATGTTCC AGGTACCGAG TCCGTATGGC CGCTTTCAGT TGAAAGCCCA   2520
ATCGGAAGGT GCGGAGAACC GAATCGATGC GCACCACATT TTGAATGGAA TCCTGATCTA   2580
GATTGTTCCT GCAGAGATGG AGAAAAATGT GCGCATCATT CCCATCATTT CTCTTTGGAT   2640
ATTGATGTTG GATGCATAGA CTTGCATGAG AACCTAGGCG TGTGGGTGGT ATTCAAGATT   2700
AAGACGCAGG AAGGTCATGC AAGACTAGGG AACCTGGAAT TTATTGAAGA GAAACCATTA   2760
TTAGGAGAAG CACTGTCTCG TGTGAAGAGA GCAGAGAAAA AATGGAGAGA CAAACGTGAA   2820
AAACTACAAT TGGAAACAAA ACGAGTATAT ACAGAGGCAA AAGAAGCTGT GGATGCTTTA   2880
TTTGTAGATT CTCAATATGA TAGATTACAA GCGGATACAA ACATTGGCAT GATTCATGCG   2940
```

| GCAGATAAAC | TTGTTCATCG | AATTCGAGAG | GCGTATCTTT | CAGAATTATC | TGTTATCCCA | 3000 |
| GGTGTAAATG | CGGAAATTTT | TGAAGAATTA | GAAGGTCGCA | TTATCACTGC | AATCTCCCTA | 3060 |
| TACGATGCGA | GAAATGTCGT | TAAAAATGGT | GATTTTAATA | ATGGATTAGC | ATGCTGGAAT | 3120 |
| GTAAAAGGGC | ATGTAGATGT | ACAACAGAGC | CATCACCGTT | CTGTCCTTGT | TATCCCAGAA | 3180 |
| TGGGAAGCAG | AAGTGTCACA | AGCAGTTCGC | GTCTGTCCGG | GGCGTGGCTA | TATCCTCCGT | 3240 |
| GTCACAGCGT | ACAAGAGGG | ATATGGAGAG | GGTTGTGTAA | CGATCCATGA | AATCGAGAAC | 3300 |
| AATACAGACG | AACTAAAATT | TAAAAACTGT | GAAGAAGAGG | AAGTGTATCC | AACGGATACA | 3360 |
| GGAACGTGTA | ATGATTATAC | TGCACACCAA | GGTACAGCAG | CATGTAATTC | CCGTAATGCT | 3420 |
| GGATATGAGG | ATGCATATGA | AGTTGATACT | ACAGCATCTG | TTAATTACAA | ACCGACTTAT | 3480 |
| GAAGAAGAAA | CGTATACAGA | TGTACGAAGA | GATAATCATT | GTGAATATGA | CAGAGGGTAT | 3540 |
| GTGAATTATC | CACCAGTACC | AGCTGGTTAT | ATGACAAAAG | AATTAGAATA | CTTCCCAGAA | 3600 |
| ACCGATAAGG | TATGGATTGA | GATTGGAGAA | ACGGAAGGGA | AGTTTATTGT | AGACAGCGTG | 3660 |
| GAATTACTCC | TTATGGAGGA | ATAG | | | | 3684 |

(2) INFORMATION FOR SEQ ID NO:8:

(i) SEQUENCE CHARACTERISTICS:
  (A) LENGTH: 1227 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:8:

```
Leu Thr Ser Asn Arg Lys Asn Glu Asn Glu Ile Ile Asn Ala Leu Ser
  1               5                  10                  15

Ile Pro Ala Val Ser Asn His Ser Ala Gln Met Asn Leu Ser Thr Asp
                 20                  25                  30

Ala Arg Ile Glu Asp Ser Leu Cys Ile Ala Glu Gly Asn Asn Ile Asp
             35                  40                  45

Pro Phe Val Ser Ala Ser Thr Val Gln Thr Gly Ile Asn Ile Ala Gly
     50                  55                  60

Arg Ile Leu Gly Val Leu Gly Val Pro Phe Ala Gly Gln Ile Ala Ser
 65                  70                  75                  80

Phe Tyr Ser Phe Leu Val Gly Glu Leu Trp Pro Arg Gly Arg Asp Pro
                 85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
210                 215                 220
```

| | | | | | | | | | | | | | | | |
|---|---|---|---|---|---|---|---|---|---|---|---|---|---|---|---|
| Arg 225 | Glu | Tyr | Ser | Asp 230 | Tyr | Cys | Ala | Arg | Trp 235 | Tyr | Asn | Thr | Gly | Leu | Asn 240 |
| Asn | Leu | Arg | Gly | Thr 245 | Asn | Ala | Glu | Ser 250 | Trp | Leu | Arg | Tyr | Asn 255 | Gln | Phe |
| Arg | Arg | Asp | Leu 260 | Thr | Leu | Gly | Val | Leu 265 | Asp | Leu | Val | Ala 270 | Leu | Phe | Pro |
| Ser | Tyr | Asp 275 | Thr | Arg | Val | Tyr | Pro 280 | Met | Asn | Thr | Ser | Ala 285 | Gln | Leu | Thr |
| Arg | Glu 290 | Ile | Tyr | Thr | Asp | Pro 295 | Ile | Gly | Arg | Thr | Asn 300 | Ala | Pro | Ser | Gly |
| Phe 305 | Ala | Ser | Thr | Asn | Trp 310 | Phe | Asn | Asn | Asn | Ala 315 | Pro | Ser | Phe | Ser | Ala 320 |
| Ile | Glu | Ala | Ala | Val 325 | Ile | Arg | Pro | Pro | His 330 | Leu | Leu | Asp | Phe | Pro 335 | Glu |
| Gln | Leu | Thr | Ile 340 | Phe | Ser | Val | Leu | Ser 345 | Arg | Trp | Ser | Asn | Thr 350 | Gln | Tyr |
| Met | Asn | Tyr 355 | Trp | Val | Gly | His | Arg 360 | Leu | Glu | Ser | Arg | Thr 365 | Ile | Arg | Gly |
| Ser | Leu | Ser 370 | Thr | Ser | Thr | His 375 | Gly | Asn | Thr | Asn | Thr 380 | Ser | Ile | Asn | Pro |
| Val 385 | Thr | Leu | Gln | Phe | Thr 390 | Ser | Arg | Asp | Val | Tyr 395 | Arg | Thr | Glu | Ser | Phe 400 |
| Ala | Gly | Ile | Asn | Ile 405 | Leu | Leu | Thr | Thr | Pro 410 | Val | Asn | Gly | Val | Pro 415 | Trp |
| Ala | Arg | Phe | Asn 420 | Trp | Arg | Asn | Pro | Leu 425 | Asn | Ser | Leu | Arg | Gly 430 | Ser | Leu |
| Leu | Tyr | Thr 435 | Ile | Gly | Tyr | Thr | Gly 440 | Val | Gly | Thr | Gln | Leu 445 | Phe | Asp | Ser |
| Glu | Thr 450 | Glu | Leu | Pro | Pro | Glu 455 | Thr | Thr | Glu | Arg | Pro 460 | Asn | Tyr | Glu | Ser |
| Tyr 465 | Ser | His | Arg | Leu | Ser 470 | Asn | Ile | Arg | Leu | Ile 475 | Ser | Gly | Asn | Thr | Leu 480 |
| Arg | Ala | Pro | Val | Tyr 485 | Ser | Trp | Thr | His | Arg 490 | Ser | Ala | Asp | Arg | Thr 495 | Asn |
| Thr | Ile | Ser | Ser 500 | Asp | Ser | Ile | Thr | Gln 505 | Ile | Pro | Leu | Val | Lys 510 | Ser | Phe |
| Asn | Leu | Asn 515 | Ser | Gly | Thr | Ser | Val 520 | Val | Ser | Gly | Pro | Gly 525 | Phe | Thr | Gly |
| Gly | Asp 530 | Ile | Ile | Arg | Thr | Asn 535 | Val | Asn | Gly | Ser | Val 540 | Leu | Ser | Met | Gly |
| Leu 545 | Asn | Phe | Asn | Asn | Thr 550 | Ser | Leu | Gln | Arg | Tyr 555 | Arg | Val | Arg | Val | Arg 560 |
| Tyr | Ala | Ala | Ser | Gln 565 | Thr | Met | Val | Leu | Arg 570 | Val | Thr | Val | Gly 575 | Gly | Ser |
| Thr | Thr | Phe | Asp 580 | Gln | Gly | Phe | Pro | Ser 585 | Thr | Met | Ser | Ala | Asn 590 | Glu | Ser |
| Leu | Thr | Ser 595 | Gln | Ser | Phe | Arg | Phe 600 | Ala | Glu | Phe | Pro | Val 605 | Gly | Ile | Ser |
| Ala | Ser 610 | Gly | Ser | Gln | Thr | Ala 615 | Gly | Ile | Ser | Ile | Ser 620 | Asn | Asn | Ala | Gly |
| Arg 625 | Gln | Thr | Phe | His | Phe 630 | Asp | Lys | Ile | Glu | Phe 635 | Ile | Pro | Ile | Thr | Ala 640 |
| Thr | Phe | Glu | Ala | Glu | Tyr | Asp | Leu | Glu | Arg | Ala | Gln | Glu | Ala | Val | Asn |

-continued

|     |     |     |     | 645 |     |     |     |     | 650 |     |     |     |     | 655 |     |
|---|---|---|---|---|---|---|---|---|---|---|---|---|---|---|---|

Ala Leu Phe Thr Asn Thr Asn Pro Arg Arg Leu Lys Thr Gly Val Thr
          660                 665                 670

Asp Tyr His Ile Asp Glu Val Ser Asn Leu Val Ala Cys Leu Ser Asp
          675                 680                 685

Glu Phe Cys Leu Asp Glu Arg Glu Leu Leu Glu Lys Val Lys Tyr
    690                 695                 700

Ala Lys Arg Leu Ser Asp Glu Arg Asn Leu Leu Gln Asp Pro Asn Phe
705                 710                 715                 720

Thr Ser Ile Asn Lys Gln Pro Asp Phe Ile Ser Thr Asn Glu Gln Ser
              725                 730                 735

Asn Phe Thr Ser Ile His Glu Gln Ser Glu His Gly Trp Trp Gly Ser
          740                 745                 750

Glu Asn Ile Thr Ile Gln Glu Gly Asn Asp Val Phe Lys Glu Asn Tyr
          755                 760                 765

Val Ile Leu Pro Gly Thr Phe Asn Glu Cys Tyr Pro Thr Tyr Leu Tyr
    770                 775                 780

Gln Lys Ile Gly Glu Ala Glu Leu Lys Ala Tyr Thr Arg Tyr Gln Leu
785                 790                 795                 800

Ser Gly Tyr Ile Glu Asp Ser Gln Asp Leu Glu Ile Tyr Leu Ile Arg
              805                 810                 815

Tyr Asn Ala Lys His Glu Thr Leu Asp Val Pro Gly Thr Glu Ser Val
          820                 825                 830

Trp Pro Leu Ser Val Glu Ser Pro Ile Gly Arg Cys Gly Glu Pro Asn
        835                 840                 845

Arg Cys Ala Pro His Phe Glu Trp Asn Pro Asp Leu Asp Cys Ser Cys
    850                 855                 860

Arg Asp Gly Glu Lys Cys Ala His His Ser His His Phe Ser Leu Asp
865                 870                 875                 880

Ile Asp Val Gly Cys Ile Asp Leu His Glu Asn Leu Gly Val Trp Val
              885                 890                 895

Val Phe Lys Ile Lys Thr Gln Glu Gly His Ala Arg Leu Gly Asn Leu
        900                 905                 910

Glu Phe Ile Glu Glu Lys Pro Leu Leu Gly Glu Ala Leu Ser Arg Val
    915                 920                 925

Lys Arg Ala Glu Lys Lys Trp Arg Asp Lys Arg Glu Lys Leu Gln Leu
930                 935                 940

Glu Thr Lys Arg Val Tyr Thr Glu Ala Lys Glu Ala Val Asp Ala Leu
945                 950                 955                 960

Phe Val Asp Ser Gln Tyr Asp Arg Leu Gln Ala Asp Thr Asn Ile Gly
              965                 970                 975

Met Ile His Ala Ala Asp Lys Leu Val His Arg Ile Arg Glu Ala Tyr
          980                 985                 990

Leu Ser Glu Leu Ser Val Ile Pro Gly Val Asn Ala Glu Ile Phe Glu
        995                 1000                1005

Glu Leu Glu Gly Arg Ile Ile Thr Ala Ile Ser Leu Tyr Asp Ala Arg
    1010                1015                1020

Asn Val Val Lys Asn Gly Asp Phe Asn Asn Gly Leu Ala Cys Trp Asn
1025                1030                1035                1040

Val Lys Gly His Val Asp Val Gln Gln Ser His His Arg Ser Val Leu
              1045                1050                1055

Val Ile Pro Glu Trp Glu Ala Glu Val Ser Gln Ala Val Arg Val Cys
          1060                1065                1070

-continued

| | | | | | | | | | | | | | | |
|---|---|---|---|---|---|---|---|---|---|---|---|---|---|---|
|Pro|Gly|Arg|Gly|Tyr|Ile|Leu|Arg|Val|Thr|Ala|Tyr|Lys|Glu|Gly|Tyr|
| |1075| | | |1080| | | | |1085| | | | |

| | | | | | | | | | | | | | |
|---|---|---|---|---|---|---|---|---|---|---|---|---|---|
|Gly|Glu|Gly|Cys|Val|Thr|Ile|His|Glu|Ile|Glu|Asn|Asn|Thr|Asp|Glu|
| |1090| | | | |1095| | | | |1100| | | |

|Leu|Lys|Phe|Lys|Asn|Cys|Glu|Glu|Glu|Val|Tyr|Pro|Thr|Asp|Thr|
|---|---|---|---|---|---|---|---|---|---|---|---|---|---|---|
|1105| | | | |1110| | | | |1115| | | |1120|

|Gly|Thr|Cys|Asn|Asp|Tyr|Thr|Ala|His|Gln|Gly|Thr|Ala|Ala|Cys|Asn|
|---|---|---|---|---|---|---|---|---|---|---|---|---|---|---|---|
| | | | |1125| | | | |1130| | | | |1135| |

|Ser|Arg|Asn|Ala|Gly|Tyr|Glu|Asp|Ala|Tyr|Glu|Val|Asp|Thr|Thr|Ala|
|---|---|---|---|---|---|---|---|---|---|---|---|---|---|---|---|
| | | |1140| | | | |1145| | | | |1150| | |

|Ser|Val|Asn|Tyr|Lys|Pro|Thr|Tyr|Glu|Glu|Glu|Thr|Tyr|Thr|Asp|Val|
|---|---|---|---|---|---|---|---|---|---|---|---|---|---|---|---|
| | |1155| | | | |1160| | | | |1165| | | |

|Arg|Arg|Asp|Asn|His|Cys|Glu|Tyr|Asp|Arg|Gly|Tyr|Val|Asn|Tyr|Pro|
|---|---|---|---|---|---|---|---|---|---|---|---|---|---|---|---|
| |1170| | | | |1175| | | | |1180| | | | |

|Pro|Val|Pro|Ala|Gly|Tyr|Met|Thr|Lys|Glu|Leu|Glu|Tyr|Phe|Pro|Glu|
|---|---|---|---|---|---|---|---|---|---|---|---|---|---|---|---|
|1185| | | | |1190| | | | |1195| | | | |1200|

|Thr|Asp|Lys|Val|Trp|Ile|Glu|Ile|Gly|Glu|Thr|Glu|Gly|Lys|Phe|Ile|
|---|---|---|---|---|---|---|---|---|---|---|---|---|---|---|---|
| | | | |1205| | | | |1210| | | | |1215| |

|Val|Asp|Ser|Val|Glu|Leu|Leu|Leu|Met|Glu|Glu|
|---|---|---|---|---|---|---|---|---|---|---|
| | | |1220| | | | |1225| | |

( 2 ) INFORMATION FOR SEQ ID NO:9:

( i ) SEQUENCE CHARACTERISTICS:
( A ) LENGTH: 1464 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

| | | | | | |
|---|---|---|---|---|---|
|ATGAAATCTA|AGAATCAAAA|TATGCATCAA|AGCTTGTCTA|ACAATGCGAC|AGTTGATAAA|60|
|AACTTTACAG|GTTCACTAGA|AAATAACACA|ATACGGAAT|TACAAAACTT|TAATCATGAA|120|
|GGTATAGAGC|CGTTTGTTAG|TGTATCAACA|ATTCAAACGG|GTATTGGTAT|TGTTGGTAAA|180|
|ATCCTTGGTA|ACCTAGGCGT|TCCTTTTGCT|GGGCAAGTAG|CTAGCCTCTA|TAGTTTTATC|240|
|CTAGGTGAGC|TTTGGCCCAA|AGGGAAAAGC|CAATGGGAAA|TCTTTATGGA|ACATGTAGAA|300|
|GAGCTTATTA|ATCAAAAGAT|ATCGACTTAT|GCAAGAAACA|AAGCACTTGC|AGATTTAAAA|360|
|GGATTAGGAG|ATGCTTTGGC|TGTCTACCAT|GAATCGCTGG|AAAGTTGGAT|TGAAAATCGC|420|
|AATAACACAA|GAACCAGAAG|TGTTGTCAAG|AGCCAATACA|TCACCTTGGA|ACTTATGTTC|480|
|GTACAATCAT|TACCTTCTTT|TGCAGTGTCT|GGAGAGGAAG|TACCACTATT|ACCAATATAT|540|
|GCTCAAGCTG|CAAATTTACA|CTTATTGCTA|TTACGAGATG|CTTCTATTTT|TGGAAAAAAT|600|
|GGGGGTTATC|AGACTCAGAA|ATTCCACAT|TTTATAATCG|CCAATCCGGG|AAATCGAAAG|660|
|AATATTCTGA|CCACTGCGTA|AAATGGTATA|ATACAGGCCT|AAATCGCTTG|ATGGGGAACA|720|
|ATGCCGAAAG|TTGGGTACGA|TATAATCAAT|TCCGTAGAGA|CATGACTTTA|ATGGTACTAG|780|
|ATTTAGTGGC|ACTATTTCCA|AGCTATGATA|CACAAATGTA|TCCAATTAAA|ACTACAGCCC|840|
|AACTTACAAG|AGAAGTATAT|ACAGACGCAA|TTGGACAGT|ACATCCGCAT|CCAAGTTTTA|900|
|CAAGTACGAC|TTGGTATAAT|AATAATGCAC|CTTCGTTCTC|TACCATAGAG|GCTGCTGTTG|960|
|TTCGAAACCC|GCATCTACTC|GATTTTCTAG|AACAAGTTAC|AATTTACAGC|TTATTAAGTC|1020|
|GATGGAGTAA|CACTCAGTAT|ATGAATATGT|GGGGAGGACA|TAAACTAGAA|TTCCGAACAA|1080|
|TAGGAGGAAC|GTTAAATACC|TCAACACAAG|GATCTACTAA|TACTTCTATT|AATCCTGTAA|1140|

```
CATTACCGTT CACTTCTCGA GACGTCTATA GGACTGAATC ATTGGCAGGG CTGAATCTAT    1200

TTTTAACTCA ACCTGTTAAT GGAGTACCTA GGGTTGATTT TCATTGGAAA TTCGTCACAC    1260

ATCCGATCGC ATCTGATAAT TTCTATTATC CAGGGTATGC TGGAATTGGG ACGCAATTAC    1320

AGGATTCAGA AAATGAATTA CCACCTGAAG CAACAGGACA GCCAAATTAT GAATCTTATA    1380

GTCATAGATT ATCTCATATA GGACTCATTT CAGCATCACA TGTGAAAGCA TTGGTATATT    1440

CTTGGACGCA TCGTAGTGCA GATC                                          1464
```

( 2 ) INFORMATION FOR SEQ ID NO:10:

( i ) SEQUENCE CHARACTERISTICS:
        ( A ) LENGTH: 488 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Met Lys Ser Lys Asn Gln Asn Met His Gln Ser Leu Ser Asn Asn Ala
 1               5                  10                  15

Thr Val Asp Lys Asn Phe Thr Gly Ser Leu Glu Asn Asn Thr Asn Thr
             20                  25                  30

Glu Leu Gln Asn Phe Asn His Glu Gly Ile Glu Pro Phe Val Ser Val
         35                  40                  45

Ser Thr Ile Gln Thr Gly Ile Gly Ile Val Gly Lys Ile Leu Gly Asn
     50                  55                  60

Leu Gly Val Pro Phe Ala Gly Gln Val Ala Ser Leu Tyr Ser Phe Ile
65                  70                  75                  80

Leu Gly Glu Leu Trp Pro Lys Gly Lys Ser Gln Trp Glu Ile Phe Met
                 85                  90                  95

Glu His Val Glu Glu Leu Ile Asn Gln Lys Ile Ser Thr Tyr Ala Arg
            100                 105                 110

Asn Lys Ala Leu Ala Asp Leu Lys Gly Leu Gly Asp Ala Leu Ala Val
        115                 120                 125

Tyr His Glu Ser Leu Glu Ser Trp Ile Glu Asn Arg Asn Asn Thr Arg
    130                 135                 140

Thr Arg Ser Val Val Lys Ser Gln Tyr Ile Thr Leu Glu Leu Met Phe
145                 150                 155                 160

Val Gln Ser Leu Pro Ser Phe Ala Val Ser Gly Glu Glu Val Pro Leu
                165                 170                 175

Leu Pro Ile Tyr Ala Gln Ala Ala Asn Leu His Leu Leu Leu Leu Arg
            180                 185                 190

Asp Ala Ser Ile Phe Gly Lys Xaa Trp Gly Leu Ser Asp Ser Glu Ile
        195                 200                 205

Ser Thr Phe Tyr Asn Arg Gln Ser Gly Lys Ser Lys Glu Tyr Ser Asp
    210                 215                 220

His Cys Val Lys Trp Tyr Asn Thr Gly Leu Asn Arg Leu Met Gly Asn
225                 230                 235                 240

Asn Ala Glu Ser Trp Val Arg Tyr Asn Gln Phe Arg Arg Asp Met Thr
                245                 250                 255

Leu Met Val Leu Asp Leu Val Ala Leu Phe Pro Ser Tyr Asp Thr Gln
            260                 265                 270

Met Tyr Pro Ile Lys Thr Thr Ala Gln Leu Thr Arg Glu Val Tyr Thr
        275                 280                 285
```

| | | | | | | | | | | | | | | |
|---|---|---|---|---|---|---|---|---|---|---|---|---|---|---|
| Asp | Ala 290 | Ile | Gly | Thr | Val | His 295 | Pro | His | Pro | Ser | Phe 300 | Thr | Ser | Thr | Thr |
| Trp 305 | Tyr | Asn | Asn | Asn | Ala 310 | Pro | Ser | Phe | Ser | Thr 315 | Ile | Glu | Ala | Ala | Val 320 |
| Val | Arg | Asn | Pro | His 325 | Leu | Leu | Asp | Phe | Leu 330 | Glu | Gln | Val | Thr | Ile 335 | Tyr |
| Ser | Leu | Leu | Ser 340 | Arg | Trp | Ser | Asn | Thr 345 | Gln | Tyr | Met | Asn | Met 350 | Trp | Gly |
| Gly | His | Lys 355 | Leu | Glu | Phe | Arg | Thr 360 | Ile | Gly | Gly | Thr | Leu 365 | Asn | Thr | Ser |
| Thr | Gln 370 | Gly | Ser | Thr | Asn | Thr 375 | Ser | Ile | Asn | Pro | Val 380 | Thr | Leu | Pro | Phe |
| Thr 385 | Ser | Arg | Asp | Val | Tyr 390 | Arg | Thr | Glu | Ser | Leu 395 | Ala | Gly | Leu | Asn | Leu 400 |
| Phe | Leu | Thr | Gln | Pro 405 | Val | Asn | Gly | Val | Pro 410 | Arg | Val | Asp | Phe | His 415 | Trp |
| Lys | Phe | Val | Thr 420 | His | Pro | Ile | Ala | Ser 425 | Asp | Asn | Phe | Tyr | Tyr 430 | Pro | Gly |
| Tyr | Ala | Gly 435 | Ile | Gly | Thr | Gln | Leu 440 | Gln | Asp | Ser | Glu | Asn 445 | Glu | Leu | Pro |
| Pro | Glu 450 | Ala | Thr | Gly | Gln | Pro 455 | Asn | Tyr | Glu | Ser | Tyr 460 | Ser | His | Arg | Leu |
| Ser 465 | His | Ile | Gly | Leu | Ile 470 | Ser | Ala | Ser | His | Val 475 | Lys | Ala | Leu | Val | Tyr 480 |
| Ser | Trp | Thr | His | Arg 485 | Ser | Ala | Asp | | | | | | | | |

BACILLUS THURINGIENSIS GENES ENCODING LEPIDOPTERAN-ACTIVE TOXINS

CROSS-REFERENCE TO RELATED APPLICATIONS

This application is a continuation-in-part of application Ser. No. 08/069,902, filed Jun. 1, 1993 now abandoned; which is a division of Ser. No. 07/759,247, filed Sep. 13, 1991, now U.S. Pat. No. 5,268,172.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner and Kim, 1988). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* var. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *B.t.* var. *israelensis* and *B.t.* var. *tenebrionis* (a.k.a. M-7, a.k.a. *B.t.* var. *san diego*), have been used commercially to control insects of the orders Diptera and Coleoptera, respectively (Gaertner, 1989). See also Couch, 1980 and Beegle, 1978. Krieg et al., 1983, describe *Bacillus thuringiensis* var. *tenebrionis*, which is reportedly active against two beetles in the order Coleoptera. These are the Colorado potato beetle, *Leptinotarsa decemlineata*, and the beetle *Agelastica alni*.

Recently, new subspecies of *B.t.* have been identified, and genes responsible for active δ-endotoxin proteins have been isolated (Höfte and Whiteley, 1989). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al., 1987, describe probes useful in classifying lepidopteran-active genes. The discovery of strains specifically toxic to other pests has been reported (Feitelson et al., 1992).

*B.t.* crystalline toxins are generally recognized as being protoxins, requiring either particular physieochemical conditions (i.e., pH, redox, ionic strength), or the action of certain proteases, or both, to generate an active toxin (Höfte and Whiteley, 1989). In most cases, the insect supplies conditions for activation of the toxin; however, cases have been documented where pre-solubilization or pre-proteolysis have been necessary for optimum activity (Jacquet et al., 1987) or detection of activity (Höfte et al., 1992).

The cloning and expression of a *B.t.* crystal protein gene in *Escherichia coli* has been described in the published literature (Schnepf and Whiteley, 1981). U.S. Pat. No. 4,448,885 and U.S. Pat. No. 4,467,036 both disclose the expression of *B.t.* crystal proteins in *E. coli*. U.S. Pat. Nos. 4,797,276 and 4,853,331 disclose *B. thuringiensis* var. *tenebrionis* (a.k.a. *B.t. san diego*, a.k.a. M-7) which can be used to control coleopteran pests in various environments. U.S. Pat. No. 4,918,006 discloses *Bacillus thuringiensis* var. *israelensis* toxins which are active against dipteran pests. This patent reports that a protein of about 27 kD, and fragments thereof, are responsible for the dipteran activity. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

BRIEF SUMMARY OF THE INVENTION

The subject invention concerns novel δ-endotoxin genes obtainable from the isolate *B.t.* PS158C2, wherein the genes encode proteins which are active against lepidopteran pests. These toxin genes can be transferred to suitable hosts as described herein.

Specifically, the invention comprises novel *B.t.* δ-endotoxin genes designated 158C2a, b, c, and d, which encode proteins active against lepidopteran pests. Further aspects of the subject invention concern lepidopteran-active toxins, and fragments thereof, encoded by the genes disclosed herein. Another embodiment of the subject invention concerns hosts transformed with the genes of the subject invention. In a preferred embodiment, the transformed hosts are plants.

BRIEF DESCRIPTION OF THE DRAWINGS

FIG. 1 is a photograph of a 9% SDS polyacrylamide gel showing alkali-soluble proteins of *Bacillus thuringiensis* PS158C2 compared to two typical lepidopteran-active strains.

BRIEF DESCRIPTION OF THE SEQUENCES

Figure 2:
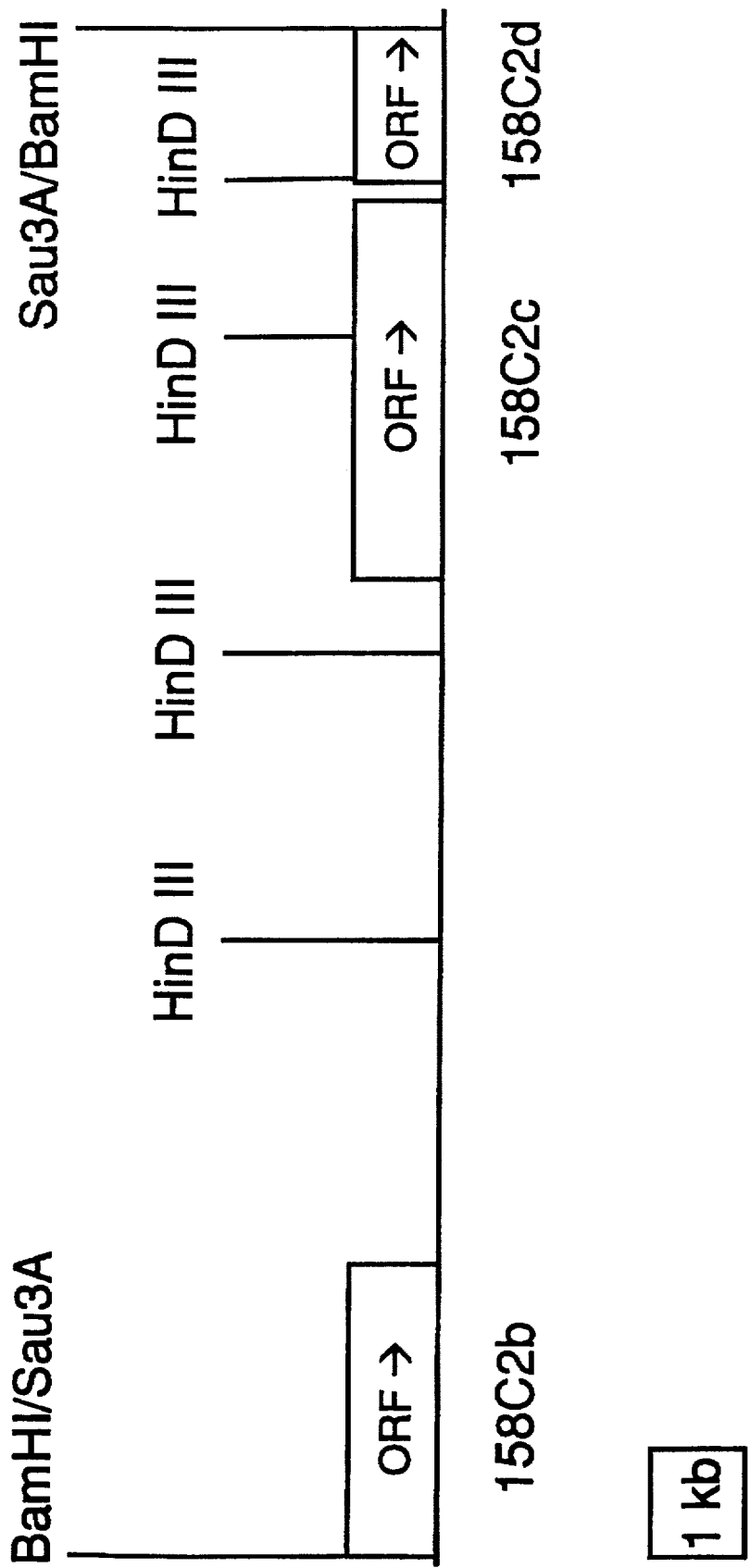
FIG. 2 is a restriction map of the DNA insert cloned in pMYC2383. Plasmid pMYC2383 contains the entire open reading frame (ORF) of the 158C2e toxin gene (SEQ ID NO. 5), the 3' portion of the 158C2b toxin gene (SEQ ID NO. 4), and the 5' portion of the 158C2d toxin gene (SEQ ID NO. 6). The approximate location of the respective genes are indicated by rectangles. The direction of transcription is indicated by an arrow for each respective gene.

SEQ ID NO. 1 is the nucleotide sequence of a "forward" oligonucleotide primer homologous to sequences conserved among numerous *B.t.* toxins.

SEQ ID NO. 2 is the nucleotide sequence of a "reverse" oligonucleotide primer homologous to sequences conserved among numerous *B.t.* toxins.

SEQ ID NO. 3 is the partial nucleotide sequence of the 158C2a toxin gene.

SEQ ID NO. 4 is the nucleotide sequence of the 158C2b toxin gene.

SEQ ID NO. 5 is the nucleotide sequence of the 158C2c toxin gene.

SEQ ID NO. 6 is the partial nucleotide sequence of the 158C2d toxin gene.

SEQ ID NO. 7 is the deduced partial amino acid sequence of the 158C2a toxin.

SEQ ID NO. 8 is the deduced amino acid sequence of the 158C2b toxin.

SEQ ID NO. 9 is the deduced amino acid sequence of the 158C2c toxin.

SEQ ID NO. 10 is the deduced amino acid sequence of the 158C2d toxin.

DETAILED DISCLOSURE OF THE INVENTION

The subject invention pertains to novel genes which encode lepidopteran-active toxins. The toxins themselves are also an important aspect of the invention. A further embodiment of the subject invention is the transformation of suitable hosts to confer upon these hosts the ability to express lepidopteran-active toxins.

Characteristics of *B.t.* PS158C2:

Colony morphology—Large colony, dull surface, typical *B.t.*

Vegetative cell morphology—typical *B.t.*

Inclusion type—Amorphic

Activity—*B.t.* PS158C2 kills all Lepidoptera tested.

Bioassay procedures and results:
  Spodoptera littoralis Bioassay—This assay was done with spray-dried powder of *B.t.* strains. First instar larvae were used with 1% agar diet containing 0.5% spray-dried powder. Mortality was read at 7 days. *B.t.* PS158C2 gave greater than 80% mortality.
  Plutella xylostella Bioassay—Dilutions of a spray-ohled powder of *B.t.* PS158C2 were incorporated in the diet, and third instar larvae were used. Mortality was read at 6 days. Rates greater than 300 µg powder per gram diet gave over 90% mortality.

TABLE 1

Comparison of B.t. PS158C2 with other lepidopteran-active strains

| Strain | Apparent protein size (SDS-PAGE) | Activity |
| --- | --- | --- |
| B.t. var. *kurstaki* | 130, 60 kDa | Lepidoptera |
| B.t. var. *aizawai* | 138, 130 kDa | Lepidoptera |
| B.t. PS158C2 | 47, 37, 34, 32 kDa | Lepidoptera |

It should be noted that the genes of the subject invention encode toxins of approximately 130 kDa. The appearance of smaller proteins upon SDS-PAGE analysis is apparently due to the breakdown of the larger toxins.

*B. thuringiensis* PS158C2, NRRL B-18872, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* PS158C2, and mutants thereof, can be used to control lepidopteran pests.

A subculture of *B.t.* PS 158C2 was deposited in the permanent collection of the Northern Research Laboratory, U.S. Department of Agriculture, Peoria, Ill., USA on Aug. 27, 1991 and was assigned the accession amber NRRL B-18872.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Genes and toxins.

The genes and toxins useful according to the subject invention include not only the full length sequences disclosed but also fragments of these sequences, variants, mutants, and fusion proteins which retain the characteristic pesticidal activity of the toxins specifically exemplified. In some instances, the fusion protein may contain, in addition to the characteristic pesticidal activity of the toxins specifically exemplified, another pesticidal activity contributed by the fusion process. As used herein, the terms "variants" or "variations" of genes refer to nucleotide sequences which encode the same toxins or which encode equivalent toxins having similar pesticidal activity. As used herein, the term "equivalent toxins" refers to toxins having the same or essentially the same biological activity against the target pests as the claimed toxins.

It should be apparent to a person skilled in this art that genes encoding lepidopteran-active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" amino acid sequence refers to sequences which have amino acid substitutions, deletions, additions, or insertions which do not materially affect the pesticidal activity of the protein.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for equivalent toxins) having the same or essentially the same pesticidal activity of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts.

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested by the pest. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is advantageous to use certain host microbes. For example, microorganism hosts can be selected which are known to occupy the pest's habitat. Microorganism hosts may also live symbiotically with a specific species of pest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of pests. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, e.g., genera Metarhizium, Bavaria, Saccharomyces, Cryptococcus, Kluyveromyces, Sporobolomyces, Rhodotorula, and Aureobasidium. Of particular interest are such bacterial species as *Pseudomonas syringae, Pseudomonas fluorescens, Serratia marcescens, Acetobacter xylinum, Agrobacterium tumefaciens, Rhodoposeudomonas spheroides, Xanthomonas campestris, Rhizobium melioti, Alcaligenes entrophus,* and *Azotobacter vinlandii;* and yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisae, Sporobolomyces roseus, S. odorus, Kluyveromyces veronae,* and *Aureoba-*

*sidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.
Treatment of cells.

As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Helly's fixative (See: Humason, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bioavailability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.
Growth of cells.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.
Formulations.

Formulated bait granules containing an attractant and spores and crystals of the *B.t.* isolates, or recombinant microbes comprising the genes obtainable from the *B.t.* isolates disclosed herein, can be applied to the environment of the pest. The bait may be applied liberally since the toxin does not affect animals or humans. Product may also be formulated as a spray or powder. Pests pick the product up on their feet or abdomen and carry it back to the nest where other pests will be exposed to the toxin. The *B.t.* isolate or recombinant host expressing the *B.t.* gene may also be incorporated into a bait or food source for the pest.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pests, e.g., plants, soil, or water by spraying, dusting, sprinkling, or the like.
Mutants.

Mutants of PS158C2 can be made by procedures well known in the art. For example, an asporogenous mutant can be obtained through ethylmethane sulfonate (EMS) mutagenesis of PS158C2. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Strain PS158C2

A subculture of B.t. strain PS158C2 can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4 \cdot 7\ H_2O$ | 2.46 g |
| $MnSO_4 \cdot H_2O$ | 0.04 g |
| $ZnSO_4 \cdot 7\ H_2O$ | 0.28 g |
| $FeSO_4 \cdot 7\ H_2O$ | 0.40 g |
| $CaCl_2$ Solution (100 ml) | |
| $CaCl_2 \cdot 2\ H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes from PS158C2

Total cellular DNA was prepared from *Bacillus thuringiensis* (*B.t.*) strain PS158C2 cells grown (Example 1) to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

An approximately 700–800 bp DNA fragment internal to novel PS158C2 130 kDa toxin genes was obtained by polymerase chain reaction (PCR) amplification using PS158C2 cellular DNA and the following primers homologous to sequences conserved among numerous *B.t.* toxins:

"Forward" 5' GGACCAGGATTTACAGG(TA)GG(AG)(AG)A 3' (SEQ ID NO. 1)

"Reverse" 5' TAACGTGTAT(AT)CG(CG)TTTTAATTT(TA)GA(CT)TC3' (SEQ NO. 2)

The amplified DNA was cloned into pBluescript S/K (Stratagene, La Jolla, Calif.) and partially sequenced by automated dideoxynucleotide DNA sequencing methodology (Applied Biosystems Incorporated). DNA sequences unique to at least two PS158C2 toxin genes (158C2a, SEQ ID NO. 3; and 158C2b, SEQ ID NO. 4) were identified by computer comparison with other known δ-endotoxin genes.

The cloned 700–800 bp DNA fragments specific to 158C2a and 158C2b were radiolabelled with a $^{32}P$ and used together in standard hybridizations of Southern blots of PS158C2 total cellular DNA. Three hybridizing HindIII fragments approximately 10 kbp, 12 kbp, and 14 kbp, respectively, were identified by the two probes. This novel array of hybridizing HindIII DNA bands contain toxin genes or restriction fragments of toxin genes from PS158C2.

A gene library was constructed from PS158C2 DNA partially digested with Sau3A. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The Sau3A inserts were ligated into BamHI-digested LambdaGem-11 (Promega, Madison, Wis.). Recombinant phage were packaged and plated on *E. coil* KW251 cells. Plaques were screened by hybridization with the individual probes described above. Hybridizing phage were plaque-purified and used to infect liquid cultures of *E. coli* KW251 cells for isolation of DNA by standard procedures (Maniatis et al.).

For subcloning the genes encoding the PS158C2 130 kDa toxins, preparative amounts of hybridizing phage DNA were digested with XhoI or SalI and electrophoresed on an agarose gel. The approximately 10–15 kbp bands containing the toxin genes were excised from the gel, electroeluted from gel slices, and purified by ion exchange chromatography as described above. The purified DNA inserts were ligated into XhoI-digested pHTBlueII (an *E. coli/B. thuringiensis* shuttle vector comprised of pBluescript S/K [Stratagene, La Jolla, Calif.] and the replication origin from a resident *B.t.* plasmid [D. Lereclus et al., 1989]). The ligation mix was used to transform frozen, competent *E. coli* NM522 cells (ATCC 47000). β-galactosidase⁻ transformants were screened by restriction digestion of alkaline lysate plasmid minipreps as above.

For the 158C2a toxin gene (SEQ ID NO. 3), an approximately 12 kbp XhoI fragment was initially subcloned from a hybridizing phage DNA preparation as above. After restriction mapping, the 158C2a toxin (SEQ ID NO. 7)was subcloned further on an approximately 9 kbp PstI-XhoI fragment in pHTBlueII. This plasmid subclone was designated pMYC2387. The partial DNA sequence for the 158C2a toxin gene (SEQ ID NO. 3) was determined by automated dideoxynucleotide sequencing using an ABI 373 sequencer and associated software.

For the 158C2b toxin gene (SEQ ID NO. 4), an approximately 15 kbp SalI fragment was subcloned from a hybridizing phage DNA preparation into pHTBlueII as above. This plasmid subclone was designated pMYC2383. Restriction endonuclease and PCR mapping revealed the presence of three toxin genes (158C2-b, -c, and -d) on the DNA insert in pMYC2383. The approximate location of toxin genes on the pMYC2383 insert is shown in FIG. 2. pMYC2383 contains the entire coding sequence for 158C2c (SEQ ID NO. 5), and incomplete, truncated genes for 158C2b (SEQ ID NO. 4) and 158C2d (SEQ ID NO. 6). Thus, the only functional toxin gene encoded on pMYC2383 is 158C2c. The DNA sequences for the full-length 158C2e toxin gene (SEQ ID NO. 5) and each of the truncated genes were determined by automated dideoxynucleotide sequencing using an ABI 373 sequencer and associated software. The sequence of the N-terminus of 158C2b toxin gene (SEQ ID NO. 4) was obtained from a phage clone containing DNA sequences overlapping those contained on pMYC2383.

Subcultures of *E. coli* NM522 containing either plasmid pMYC2387 (strain MR644) or pMYC2383 (strain MR645) were deposited in the permanent collection of the Patent Culture Collection (NRRL), Regional Research Center, 1815 North University Street, Peoria, Ill. 61604 USA on 11 Apr. 1995. The accession numbers are:

| Strain | Accession number |
| --- | --- |
| MR644 | NRRL B-21427 |
| MR645 | NRRL B-21428 |

To express the 158C2c toxin (SEQ ID NO. 9), pMYC2383 was introduced into the acrystalliferous (Cry⁻) *B.t.* host, CryB (A. Aronson, Purdue University, West Lafayette, Ind.), by electroporation. Expression of the 130kDa 158C2c toxin (SEQ ID NO. 9) in sporulating cultures was demonstrated by SDS-PAGE analysis.

EXAMPLE 3

Insertion of Toxin Genes Into Plants

One aspect of the subject invention is the transformation of plants with genes coding for a toxin active against lepidopteran pests. The transformed plants are resistant to attack by lepidopterans.

Genes encoding lepidopteran-active toxins, as disclosed herein, can be inserted into plant cells using a variety of techniques which are well known in the art. Those techniques include transformation with T-DNA using *Agrobacterium tumefaciens* or *Agrobacterium rhizogenes* as transformation agent, fusion, microinjection, bombardment, chemical agent (PEG) assisted DNA uptake, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of microinjection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 4

Cloning of Novel *B.t.* Genes Into Insect Viruses

A number of viruses are known to infect insects. These viruses include, for example, baculoviruses and entomopoxviruses. In one embodiment of the subject invention, lepidopteran-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Patents

U.S. Pat. No. 4,448,885.
U.S. Pat. No. 4,467,036.
U.S. Pat. No. 4,695,455
U.S. Pat. No. 4,695,462.
U.S. Pat. No. 4,797,276.
U.S. Pat. No. 4,849,217.
U.S. Pat. No. 4,853,331.
U.S. Pat. No. 4,918,006.
U.S. Pat. No. 4,948,734.
U.S. Pat. No. 5,135,867.
U.S. Pat. No. 5,151,363.

Other References

Beegle, C. C., (1978) "Use of Entomogenous Bacteria in Agroecosystems," *Developments in Industrial Microbiology* 20:97–104.

Couch, T. L. (1980) "Mosquito Pathogenicity of *Bacillus thuringiensis* var. *israelensis*," *Developments in Industrial Microbiology* 22:61–76.

Feitelson, J. S., J. Payne, L. Kim (1992) *Bio/Technology* 10:271–275.

Gaertner, F. H. (1989) "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.

Gaertner, F. H., L. Kim (1988) *TIBTECH* 6:S4–S7.

Höfte, H., H. R. Whiteley (1989) *Microbiological Reviews* 52(2):242–255.

Höfte, H. R., K. Annys, B. Lambert, S. Jansens, P. Soetaert, M. Peferoen (1992) "Novel *Bacillus thuringiensis* insecticidal crystal protein with a silent activity against coleopteran larvae," *Appl. Environ. Microbiol.* 58:2536–2542.

Humason, Gretchen L., *Animal Tissue Techniques*, W. H. Freeman and Company, 1967.

Jacquet, J., R. Hutter, P. Luthy (1987) "Specificity of *Bacillus thuringiensis* delta-endotoxin," *Appl. Environ. Microbiol.* 53:500–504.

Krieg, A., A. M. Huger, G. A. Langenbruch, W. Schnetter (1983) *Z. ang. Ent.* 96:500–508.

Lereclus, D. et al. (1989) *FEMS Microbiology Letters* 60:211–218.

Maniatis, T., E. F. Fritsch, J. Sambrook (1982) *Molecular Cloning: A Laboratory Manual*, Cold Spring Harbor Laboratory, Cold Spring Harbor, N.Y.

Pfannenstiel, M. A., E. J. Ross, V. C. Kramer, K. W. Nickerson (1984) *FEMS Microbiol. Lett.* 21:39.

Prefontaine, G., P. Fast, P. C. K. Lau, M. A. Hefford, Z. Hanna, R. Brosseau (1987) *Appl. Environ. Microbiol.* 53(12):2808–2814.

Reichenberg, D., in *Ion Exchangers in Organic and Biochemistry* (C. Calmon and T. R. E. Kressman, eds.), Interscience, New York, 1957.

Schnepf, H. E., H. R. Whiteley (1981) *Proc. Natl. Acad. Sci. USA* 78:2893–2897.

Singh, G. J. P., S. Gill (1985) "Myotoxic and Neurotoxic Activity of *Bacillus thuringiensis* var. *israelensis* Crystal Toxin," *Pesticide Biochemistry and Physiology* 24:406–414.

---

We claim:

1. An isolated polynucleotide sequence encoding a lepidopteran-active toxin wherein said toxin comprises SEQ ID NO. 7, 8, or 9, or a lepidopteran-active variant or portion thereof wherein said variant has at least 90% sequence identity with SEQ ID NO. 7, 8, or 9.

2. The polynucleotide sequence, according to claim 1, which encodes a toxin comprising SEQ ID NO. 7.

3. The polynucleotide sequence, according to claim 2, comprising SEQ ID NO. 3.

4. The polynucleotide sequence, according to claim 1, which encodes a toxin of SEQ ID NO. 8.

5. The polynucleotide sequence, according to claim 4, which is shown in SEQ ID NO. 4.

6. The polynucleotide sequence, according to claim 1, which encodes a toxin of SEQ ID NO. 9.

7. The polynucleotide sequence, according to claim 6, which is shown in SEQ ID NO. 5.

8. An isolated polynucleotide sequence which encodes a protein toxic to lepidopteran pests, wherein said toxin is encoded by a polynucleotide sequence that can be amplified using SEQ ID NO. 1 and SEQ ID NO. 2 as primers and wherein said polynucleotide sequence encodes a toxin selected from the group consisting of SEQ ID NO. 7, SEQ ID NO. 8, SEQ ID NO. 9, and lepidopteran-active fragments thereof.

9. The polynucleotide sequence, according to claim 8, which comprises a polynucleotide sequence selected from the group consisting of SEQ ID NO. 3, SEQ ID NO. 4, and SEQ ID NO. 5.

10. A recombinant host transformed by a polynucleotide sequence of claim 1, wherein said recombinant host expresses a lepidopteran-active toxin.

11. The recombinant host, according to claim 10, wherein said host is a plant.

* * * * *

UNITED STATES PATENT AND TRADEMARK OFFICE
CERTIFICATE OF CORRECTION

PATENT NO. : 5,723,758

DATED : March 3, 1998

INVENTOR(S) : Payne et al.

It is certified that error appears in the above-indentified patent and that said Letters Patent is hereby corrected as shown below:

Column 1, line 59: "physieochemical" should read --physicochemical--.

Column 2, line 47: "158C2e" should read --158C2c--.

Column 3, lines 34-35: "spray-oh-led" should read --spray-dried--.

Column 4, line 3: "PS       158C2" should read --PS158C2--; and line 6: "accession amber" should read --accession number--.

Column 10, line 27: "(SEQ NO. 2)" should read --(SEQ ID NO. 2)--; and line 65: "shuffle" should read --shuttle--.

Column 11, line 27: "158C2e" should read --158C2c--.

Signed and Sealed this

Fourth Day of August, 1998

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,723,758

DATED : March 3, 1998

INVENTOR(S) : Payne *et al.*

It is certified that error appears in the above-identified patent and that said Letters Patent is hereby corrected as shown below:

Columns 17-18, in Section 2 (8th line of text) "SEQ ID NO:4:" should read --SEQ ID NO:7:--.

Columns 17-18, in Section 2 (15th line of text) "SEQ ID NO:4:" should read --SEQ ID NO:7:--.

Columns 21-22, in Section 2 (5th line of text) "SEQ ID NO:5:" should read --SEQ ID NO:4:--.

Columns 21-22, in Section 2 (12th line of text) "SEQ ID NO:5:" should read --SEQ ID NO:4:--.

Columns 23-24, in Section 2 (29th line of text) "SEQ ID NO:6:" should read --SEQ ID NO:8:--.

Columns 23-24, in Section 2 (36th line of text) "SEQ ID NO:6:" should read --SEQ ID NO:8:--.

Columns 29-30, in Section 2 (33rd line of text) "SEQ ID NO:7:" should read --SEQ ID NO:5:--.

Columns 29-30, in Section 2 (40th line of text) "SEQ ID NO:7:" should read --SEQ ID NO:5:--.

UNITED STATES PATENT AND TRADEMARK OFFICE
CERTIFICATE OF CORRECTION

PATENT NO. : 5,723,758
DATED : March 3, 1998
INVENTOR(S) : Payne et al.

It is certified that error appears in the above-identified patent and that said Letters Patent is hereby corrected as shown below:

Columns 33-34, in Section 2 (14th line of text) "SEQ ID NO:8:" should read --SEQ ID NO:9:--.

Columns 33-34, in Section 2 (21st line of text) "SEQ ID NO:8:" should read --SEQ ID NO:9:--.

Columns 39-40, in Section 2 (21st line of text) "SEQ ID NO:9:" should read --SEQ ID NO:6:--.

Columns 39-40, in Section 2 (28th line of text) "SEQ ID NO:9:" should read --SEQ ID NO:6:--.

Signed and Sealed this

Twentieth Day of April, 1999

Attest:

Q. TODD DICKINSON

*Attesting Officer*  *Acting Commissioner of Patents and Trademarks*